(12) United States Patent
Windisch et al.

(10) Patent No.: US 7,915,220 B2
(45) Date of Patent: Mar. 29, 2011

(54) PEPTIDOMIMETIC AGENTS FROM DEXTROROTATORY AMINO ACIDS AS WELL AS PHARMACEUTICAL AGENTS THAT CONTAIN THE LATTER FOR TREATMENT OF NEURODEGENERATIVE DISEASES

(75) Inventors: Manfred Windisch, St. Radegund (AT); Birgit Hutter-Paier, Graz (AT); Robert Wronski, Graz (AT)

(73) Assignee: JSW-Research Forschungslabor GmbH, Graz (AT)

( * ) Notice: Subject to any disclaimer, the term of this patent is extended or adjusted under 35 U.S.C. 154(b) by 437 days.

(21) Appl. No.: 11/950,539

(22) Filed: Apr. 14, 2008

(65) Prior Publication Data

US 2008/0200397 A1     Aug. 21, 2008

(30) Foreign Application Priority Data

Dec. 6, 2006   (AT) .............................. A 2025/2006

(51) Int. Cl.
*A61K 38/08* (2006.01)
*C07K 7/06* (2006.01)

(52) U.S. Cl. ...... 514/8.3; 514/17.8; 514/21.7; 514/21.8; 530/329

(58) Field of Classification Search .......................... None
See application file for complete search history.

(56) References Cited

U.S. PATENT DOCUMENTS

| 2005/0287565 A1 | 12/2005 | Merchiers et al. |
| 2006/0036073 A1 * | 2/2006 | Windisch ...................... 530/326 |
| 2009/0286745 A1 * | 11/2009 | Zurdo et al. .................... 514/15 |

FOREIGN PATENT DOCUMENTS

| WO | 03/082906 | * 10/2003 |
| WO | WO 2005/023858 | 3/2005 |

OTHER PUBLICATIONS

Fischer 2003 (Current Protein and Peptide Science 4:339-356).*
Taylor et al. 2000 Journal of Pharmacology and Experimental Therapeutics 295:190-194.*

* cited by examiner

*Primary Examiner* — Daniel E Kolker
(74) *Attorney, Agent, or Firm* — Young & Thompson

(57) ABSTRACT

A peptidomimetic agent from dextrorotatory amino acids includes vGek with Dval-gly-Dglu-Dlys as a central D-amino acid sequence, whereby gly is equal to D-glycine, which is equal to L-glycine. Pharmaceutical agents for use in the treatment of neurodegenerative diseases, in particular Alzheimer's disease, Parkinson's disease, Lewy Body dementia, Creutzfeldt-Jakob disease, as well as Huntington's Chorea disease, multi-system atrophy as well as disorders similar to these neurodegenerative diseases that contain at least one peptidomimetic agent from dextrorotatory amino acids are also included.

12 Claims, 1 Drawing Sheet

PEPTIDOMIMETIC AGENTS FROM DEXTROROTATORY AMINO ACIDS AS WELL AS PHARMACEUTICAL AGENTS THAT CONTAIN THE LATTER FOR TREATMENT OF NEURODEGENERATIVE DISEASES

The invention relates to peptidomimetic agents from dextrorotatory amino acids as well as pharmaceutical agents that contain the latter for treatment of neurodegenerative diseases.

BACKGROUND OF THE INVENTION

In recent years, a number of peptides were found that were suitable for various pharmaceutical agent applications. In most cases, however, peptides cannot be taken orally, since they are often already metabolized or in turn are very quickly excreted from the body before reaching the site of action.

Peptidomimetic agents are peptide-like structures that can imitate or inhibit peptide actions as ligands. They are distinguished by a higher stability, by which the probability increases of reaching the site of action and exerting there an action as a pharmaceutical agent.

Aggregates that consist of incorrectly folded proteins very frequently occur in the course of neurodegenerative diseases. In the case of Alzheimer's disease, the extracellular deposits that are known as "plaques" from the literature, which mainly consist of β-amyloid, represent a main feature. The neurofibrillary bundles that occur intracellularly and mainly consist of hyperphosphorylated Tau protein are another feature.

The investigation of β-amyloid plaque as well as the combatting of the same has occupied a central role in the research of Alzheimer's disease in recent years.

At this time, no treatment that acts on the causes of disease is available for treating Alzheimer's disease, Parkinson's disease, Lewy Body dementia or other neurodegenerative diseases. The drug target that is best known and best developed at this time for treating Alzheimer's disease deals with the β-amyloid-induced development of plaque. Alzheimer's disease affects 15 million humans in Europe and in the U.S.A. The incidence is 1-2% and increases to about 4% in the ninth decade of life.

The deposits in the form of plaque mainly consist of amyloidogenic β-amyloid. This amyloidogenic molecule species is formed by processing the amyloid-precursor protein (APP) (Kang et al., Nature, 325 (6106): 733-6, 1987; Goldgaber et al., J Neural Transm Suppl. 24: 23-28, 1987). APP, a transmembrane protein, whose physiological function is still not completely clarified (Selkoe, J Alzheimer's Dis., 3(1): 75-80, 2001), is present everywhere in the organism, but primarily in neuronal cells.

During and after the transport of the APP by the secretory pathway, the protein can be cleaved in various ways (Goate et al., Nature, 349 (6311): 704-6, 1991). The corresponding proteolytic activities are named α-, β-, or γ-secretase. The activity of the α-secretase results in the cleavage of the soluble, extracellular portion of the protein (Esch et al., Science, 248 (4959): 1122-4, 1990). In this case, the transmembrane portion remains (non-amyloidogenic pathway). Another path of the processing contains the cleavage by β- and γ-secretase (amyloidogenic pathway). The cleavage by the β-secretase activity results in a somewhat smaller secreted fragment (β-APPs) and a larger transmembrane portion (C-99). The C-99 fragment is then cleaved by the γ-secretase activity within the transmembrane portion. The amyloidogenic Aβ-peptides with 40 or 42 amino acids (Aβ1-40, 1-42) result from this cleavage, which can be carried out primarily on two sites.

Aβ-1-42 has a strong tendency to form β-folded-sheet structures, which are almost impervious to degradation by natural means. β-Folded-sheet structures have a very strong tendency to form fibrils and ultimately turn into large aggregates.

In addition to the strong tendency toward aggregation, Aβ-1-42 is distinguished in particular by a pronounced toxicity. Among other things, the presence of Aβ1-42 leads to an increase of oxidative stress as well as increased lipid peroxidation (Butterfield, D. A., Free Radic Res. 2002 December; 36 (12): 1307-13).

Aβ1-42 disrupts the functionality of the synapses and results in excitotoxicity by a disruption of the cellular calcium balance. By the already mentioned lipid peroxidation, it results in the production of toxic oxidation products, which disrupt the functionality of ATPases, glutamate and glucose transporters (Mattson, M. P. and Chan S, L., Cell Calcium. 2003 October-November; 34 (4-5): 385-97). The result is a loss of nerve cells by necrosis or apoptosis.

A number of in-vivo and in-vitro models, which impressively confirm the role of Aβ1-42 in connection with neurodegeneration, exist. In transgenic mouse models, behavior deficits were also clearly attributable to Aβ31-42.

The U.S. Pat. No. 5,985,242 describes retroinverse sequences that consist of D-amino acids, derived from the amino acid range 17-21 of β-amyloid. The molecules described there influence the aggregation of β-amyloid.

WO-03/082906 A discloses peptides that are derived from N-terminal sequences of the β-synuclein and exert protective action relative to the neurotoxicity of β-amyloid.

The direct prevention of the aggregation behavior of β-amyloid by sequences that are directly derived from β-amyloid protein, as proposed in U.S. Pat. No. 5,985,242, involves the risk, however, of additional complications, since, as already known per se, small amyloid-like peptides can be directly neurotoxic. However, the inhibition of the neurotoxicity exerted by already aggregated Aβ1-42 (i.e., without explicit influence of the aggregation behavior) could even offer a great advantage. The peptides built up to form L-amino acids and described in WO 03/082906 A meet this requirement, but have a stability that is not quite optimum for use as pharmaceutical agents.

SUMMARY OF THE INVENTION

The object according to the invention was thus to find peptidomimetic agents that exert specific protection against amyloid-mediated neurotoxicity, but have no similarities to the amino acid sequence in β-amyloid regardless of the direction in which they are read.

DETAILED DESCRIPTION OF THE INVENTION

Figure 1:
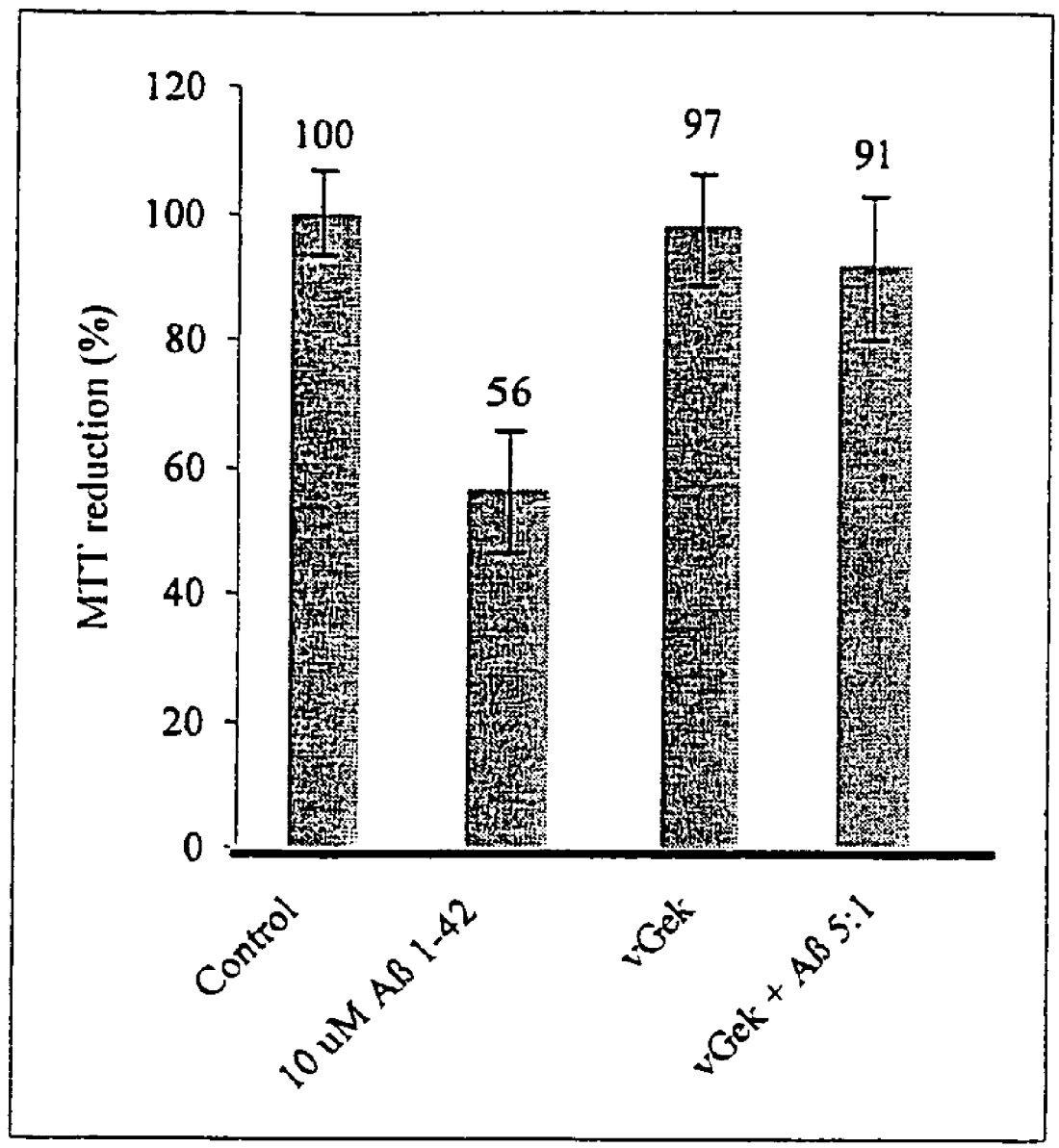
FIG. 1 shows the results of an MTT test with the nuclear sequence of vGEK.

According to the invention, a peptidomimetic agent from dextrorotatory amino acids is proposed, which is characterized in that it comprises vGek with Dval-gly-Dglu-Dlys as a central D-amino acid sequence, whereby gly is equal to D-glycine, which is equal to L-glycine. Additional advantageous configurations of this peptidomimetic agent according to the invention are disclosed according to subclaims.

Moreover, the invention comprises pharmaceutical agents for use in the treatment of neurodegenerative diseases, in particular Alzheimer's disease, Parkinson's disease, Lewy Body dementia, Creutzfeldt-Jakob disease, as well as Huntington's Chorea disease, multi-system atrophy as well as disorders similar to these neurodegenerative diseases that contain at least one peptidomimetic agent from dextrorotatory amino acids, which comprises vGek with Dval-gly-Dglu-Dlys as a central D-amino acid sequence, whereby gly is equal to D-glycine, which is equal to L-glycine.

Other advantageous configurations of the pharmaceutical agent according to the invention are disclosed according to subclaims.

Furthermore, the invention relates to the use of the peptidomimetic agents according to the invention for the production of a pharmaceutical agent for use in the treatment of neurodegenerative diseases, in particular Alzheimer's disease, Parkinson's disease, Lewy Body dementia, Creutzfeldt-Jakob disease, as well as Huntington's Chorea disease, multi-system atrophy as well as disorders that are similar to these neurodegenerative diseases.

An essential advantage of the peptidomimetic agents according to the invention, which consist of D-amino acids as well as glycine, is the higher stability compared to the degradation by various enzymes that occur in the body—in particular peptidases. For this reason, the stability of the nuclear sequence mimetic agent vGek was compared to that of the corresponding retroinverse peptide KEGV according to WO 03/082906 A, whereby the peptides together with a rat brain homogenate were incubated for 15 minutes as well as for 1, 3 and 24 hours.

To this end, freshly isolated rat brain was homogenized in tris buffer (pH 7.6) and used immediately. In each case, a portion of a 1 mmol peptide solution and four parts of the homogenate were incubated at 37° C. After the incubation, the decomposition of the enzymes was halted by adding 50 µl of 0.1 M HCl. Then, a denaturation of the proteins was carried out with methanol (volume ratio: 1:4) at −20° C. for 60 minutes. Then, it was centrifuged for 20 minutes at 4° C. and 29,000 g.

Finally, the samples were concentrated under vacuum and analyzed by means of RP-HPLC (liquid chromatography, with UV/vis detector, detection wavelength: 220 nm; solvent: (A) 0.1% TFA/water (A), 0.1% TFA in 80% ACN/water (B); column: Phenomenex Jupiter C18 (250×4 mm, 5 µm of 300 Å), flow rate: 1.2 ml/minute, gradients: 0 to 15% B after 30 minutes ($KEGV_{OH}$), 0% isocratic B for 10 minutes, then at 0 to 15% B after 30 minutes ($KEGV_{NH2}$), 0 to 15% B after 20 minutes ($vGek_{NH2}$)).

As an alternative, LC-MS (Applied Biosystems 140C Microgradient System; solvent: 0.1% HCOOH/water (A), 0.1% HCOOH in 80% acetonitrile/water (B); column: Alltech Hypersil C18 (150×2.1 mm, 5 µm of 100 Å), flow rate: 0.15 ml/minute, gradient: 0 to 15% B after 20 minutes; detector: Finnigan TSQ-7000 Triple Quadrupole Mass Spectrometer, m/z Range; 10-1000, scan time: 1.0 second) was also used.

It was finally confirmed that the peptide KEGV is comparatively quickly degraded both in amidated form and also in non-amidated form. After as little as 15 minutes, only about 50% of the substance used is left, and after one hour, complete KEGV can no longer be detected. The nuclear sequence of the mimetic agent vGek, however, has a significantly higher enzyme resistance: barely after 24 hours, $vGek_{NH2}$ can be detected in the test batch.

| Sample | $T_{1/2}$ | 15 Minutes | 1 Hour | 3 Hours | 24 Hours |
|---|---|---|---|---|---|
| $KEGV_{OH}$ | <15 Minutes | 14% | 0% | 0% | 0% |
| $KEGV_{NH2}$ | <15 Minutes | 22% | 0% | 0% | 0% |
| $vGek_{NH2}$ | 20-24 Hours | — | — | 70% | 50% |

The respective half-lives ($t_{1/2}$) of the examined peptides can be read from the table. In columns 3 to 6, it is possible to read what portion of the amount of sample used is left after 15 minutes, and it was still detectable after 1, 3 and 24 hours. It is evident from this that under the selected in vitro conditions, which represent an approximation on the ratios in the brain, the stability of the peptidomimetic agent vGek according to the invention is around 2-3 orders of magnitude above that of the corresponding peptide KEGV.

To examine the action of the peptidomimetic agent according to the invention in a relevant biological system, injury tests were performed in cell cultures with Aβ-1-42 (β-amyloid). Differentiated SHSY-5Y cells were used as cell culture systems.

The cells that were still not differentiated were cultivated in 96-well plates at 37° C. in an atmosphere in DMEM/F12 (Cambrex) that contains 5% $CO_2$ until confluence is completed. For differentiation, the following medium composition was selected: 10 µmol of All-Trans-retinoic acid, 10% FBS, 4 mmol of L-glutamine, 200 units/ml of penicillin, 200 µg/ml of streptomycin, 0.5% DMSO in MEM non-essential amino acids (e.g., Cambrex). After 8 days in the differentiation medium, $3×10^5$ cells/cm² in the form of a monolayer were present.

Before the application, the test substances were irradiated for 10 minutes in a form already dissolved in culture medium. This medium contained 2% FBS (fetal bovine serum) and was free of phenol red, retinoic acid and DMSO.

Aβ-1-42 was pre-aggregated before the addition for 24 hours at room temperature while being shaken lightly.

To damage the cells, the differentiation medium was drawn off and replaced by new medium, which contained 2% FBS, 10 µmol of aggregated Aβ-1-42 as well as 50 µmol each of the peptide to be tested.

To determine the number of surviving cells, 40 µg of 3-(4, 5-dimethylthiazol-2-yl)-2,5-diphenol tetrazolium-bromide (MTT) was added per well and incubated for 3 hours at 37° C. Regarding the principle of the method: only living cells can turn yellow MTT into blue-colored formazan crystals.

Then, the medium was carefully emptied, and the formazan crystals that were produced were dissolved with a DMSO/ethanol solution (4:1). Finally, the color intensity obtained was measured at 550 nm in an ELISA reader.

The properties of the nuclear sequence vGek were examined with an MTT test on the survival rate of SHSY-5Y cells.

From this, it can be seen that the survival rate in the presence of 10 µmol of pre-aggregated Aβ-1-42 drops to 56%. The third column, which is referred to as vGek, shows that vGek at a concentration of 50 µmol has no detectable influence on the survival of cells. Based on the extreme righthand column (vGek+Aβ 5:1), it can be shown that 50 µmol of the peptidomimetic agent vGek cannot drop the survival rate despite the presence of 10 µmol of Aβ-1-42. This means in toto that the nuclear sequence vGek in the concentration that is used is not toxic, but is able to almost completely prevent the damage of the SHSY-5Y cells produced by Aβ-1-42.

The chemical synthesis of a peptide from D-amino acids as well as also the production of the nuclear sequence vGek can be performed with conventional processes, for example with the Merrifield Solid Phase Synthesis Technology (Merrifield, J. Am. Chem. Soc., 85: 2149-2154, 1963; Kent et al., Synthetic Peptides in Biology and Medicine, 29 ff eds Alitalo et al., Elsevier Science Publishers 1985; Haug, J. D., Peptide Synthesis and the Protecting Group Strategy, American Biotechnology Laboratory, 5 (1), 40-47, 1987). The processes for chemical peptide synthesis also comprise the use of automatic peptide syntheses with use of commercially available protected amino acids, such as, for example, Biosearch (Model 9500 and 96001), Applied Biosystems Inc. (Model 430), Miligen (Model 9050), etc.

For the production of the peptidomimetic agents that are expanded around the nuclear sequence, as disclosed according to claim 3, the usual derivatization is carried out at the C-terminal and/or N-terminal end of the nuclear sequence VgeK.

Thus, lysine and the amino-terminal end can be derivatized with succinate or other carboxylic acid anhydrides. These reactions have the effect that the charge of the lysinyl radical is reversed. Other suitable reagents for derivatization of alpha-amino-containing radicals comprise imido-esters, such as methyl-bicolinimidate, pyridoxal-phosphate, pyridoxal, chloroborohydride, trinitrobenzenesulfonic acid, O-methylisourea, 2,4-pentanedione and transaminase-catalyzed reactions with glyoxylate.

Free carboxyl-side groups (e.g., glutamyl) can be selectively modified by reaction with carbodimides (R'—N—C—N—R'), such as 1-cyclohexyl-3-(2-morpholinyl (4-ethyl)) carbodimide or 1-ethyl-3-(4-azonia-4,4-dimethylpentyl)-carbodiimide.

Other modifications include the hydroxylation of lysine, the methylation of the $\alpha$-amino group of lysine and arginine, as well as the acetylation of the N-terminal amino group and the amidation of the C-terminal carboxyl groups. Examples of such derivatizations are the formyl, acetyl and propionyl amides as well as the methyl amides and dimethyl amides. All methods that are mentioned here for derivatization are familiar to the peptide chemist.

In general, the compounds according to the invention are administered in therapeutically effective amounts in connection with pharmaceutically acceptable vehicles or solvents. Such vehicles comprise, for example, physiological common salt solutions, buffered common salt solutions, dextrose, water, glycerol, ethanol and combinations thereof. The respective formulation is to be matched to the type of administration.

The composition can also contain, if necessary, varying amounts of moisture donors or emulsifiers or pH-buffering substances. The pharmaceutical composition can be a liquid solution, a suspension, an emulsion, a tablet, a pill, a capsule, a retard formulation or a powder. The preparation can also be produced as a suppository with common binders and vehicles, such as triglycerides. Oral formulations can contain standard vehicles, such as mannitol, lactose, starch, magnesium stearate, sodium saccharine, cellulose, magnesium carbonate and others in pharmaceutical purity. Various administration systems are known and can be used to ensure the therapeutic application of the substances according to the invention, such as, e.g., the encapsulation in liposomes, microparticles and microcapsules.

The form of administration is prepared in accordance with the processes that are common in pharmaceutics, for an intravenous administration in humans or other mammals. Typically, the compositions for intravenous administration are present in the form of a sterile, isotonic, aqueous buffer solution. If necessary, the preparation can also contain solubilizers and locally active anesthetics to alleviate the pain at the injection site.

In general, the components are made available either separately or mixed in a metering unit, for example as a dry, freeze-dried powder or anhydrous concentrate in a hermetically sealed container, such as an ampoule, on which the amount of the active pharmaceutical agent active ingredient is recorded.

If the dispensing form can be administered as an infusion, it can be dissolved in an infusion flask, which contains sterile water or salt solution in pharmaceutical purity. If the preparation is to be administered by injection, an ampoule with sterile water for injection purposes or common salt solution can be made available so that the individual components can be mixed according to directions before administration.

The therapeutic substances, which are described in this application, can be formulated both in free form and as pharmaceutically compatible salt. Pharmaceutically compatible salts are those that were formed with free amino groups, e.g., those that originate from hydrochloric acid or oxalic acid and those that are formed with free carboxyl groups, such as those of sodium, potassium, ammonium, calcium, iron oxides, isopropylamine, triethylamine, 2-ethylaminoethanol, histidine, procaine, etc.

The amount of the pharmaceutical agent that is described in this invention must be effective for the treatment of the special disease or condition; this depends on the type and the degree and is determined by standardized clinical processes.

Thus, based on tests on rats, it was demonstrated that the peptidomimetic agents according to the invention pass through the blood-brain barrier, although these are occasionally long-chain, i.e., bulky molecules. The test was performed as follows:

Rats were injected with 2.94 mmol of tritiated vGek (vGek of specific activity: 34.0 Ci/mmol). 10, 30 and 60 minutes after the injection, the animals were anesthetized, and blood as well as a few organs were removed for examination and weighed. Depending on the organ, 50-250 mg of tissue was removed in a solvent and incubated at 60° C. for 2 hours. After cooling to room temperature, 200 μl of 30% $H_2O_2$ was added. Then, another incubation at 60° C. was carried out for 30 minutes. Finally, the radioactivity was determined with the aid of a scintillation measuring device.

Result:

The radioactivity reached its maximum in the brain after 30 minutes. The highest measured value in the brain was 1.33 pmol. It can be assumed from this that vGek could overcome the blood-brain barrier.

The exact dose, which must be used according to the invention, also depends on the type of administration and the degree of severity of the disease or the disorder. This amount should be adapted with allowance for the specific circumstances of the patient, based on the attending physician's assessment. Suitable dosage ranges for intravenous administration are in general between 20-4,000 μg of the active component per kg of body weight. Suitable dosages for intranasal applications are in the range of between 0.01 mg per kg of body weight up to 1 mg per kg of body weight. Effective dosages for oral applications are in the range of 1 mg to 1,000 mg per kg of body weight and day. The effective dosages are extrapolated from the dose-action curves, which are derived from in vitro models or animal model test systems.

In summary, it can be stated that the peptidomimetic agents according to the invention from dextrorotatory amino acids and glycine are stable against enzymatic destruction; this is produced by the dextrorotatory form of the amino acids, whereby gly equals D-glycine, which is equal to L-glycine. An elevated stability in the metabolism and accordingly a target-oriented action on the desired site of action can thus be produced. The peptidomimetic agents according to the invention that contain pharmaceutical agents can inhibit at least the further build-up of the plaques that occur in neurodegenerative diseases and are therefore relatively free of side effects, since the nuclear sequence vGek shows no toxic effects in the organism whatsoever.

The invention claimed is:

1. A peptidomimetic agent from dextrorotatory D-amino acids comprising a central nuclear sequence vGek with Dval-gly-Dglu-Dlys, whereby gly equals D-glycine, which is equal to L-glycine, wherein, the central nuclear sequence is expanded on its N-terminal and/or C-terminal end by additional dextrorotatory D-amino acids, and selected from the group:

rervGek, vGekrer, ervGek, revGek, vGeker, and vGekre, whereby r =D-arginine, e =D-glutaminic acid, v =D-valine, G =D-glycine =L-glycine, k =D-lysine.

2. A pharmaceutical agent for treatment of Alzheimer's disease comprising at least one of the peptidomimetic agents according to claim 1 as an active ingredient.

3. A pharmaceutical agent according to claim 2, wherein the pharmaceutical agent is prepared for oral administration.

4. A pharmaceutical agent according to claim 2, wherein the pharmaceutical agent is prepared for rectal administration.

5. A pharmaceutical agent according to claim 2, wherein the pharmaceutical agent is prepared for administration by inhalation.

6. A pharmaceutical agent according to claim 2, wherein the pharmaceutical agent is prepared for transdermal administration.

7. A pharmaceutical agent according to claim 2, wherein the pharmaceutical agent is prepared for transmucosal administration.

8. A pharmaceutical agent according to claim 2, wherein the pharmaceutical agent is prepared for administration with the aid of implants that contain active ingredients.

9. A pharmaceutical agent according to claim 2, wherein the pharmaceutical agent is prepared for intracerebroventricular administration.

10. A pharmaceutical agent according to claim 2, wherein the pharmaceutical agent is prepared for administration by injection.

11. A pharmaceutical agent according to claim 2, wherein the pharmaceutical agent is prepared for transnasal administration.

12. A pharmaceutical agent according to claim 2, wherein the pharmaceutical agent is prepared for administration by infusion.

* * * * *

UNITED STATES PATENT AND TRADEMARK OFFICE
CERTIFICATE OF CORRECTION

PATENT NO. : 7,915,220 B2  
APPLICATION NO. : 11/950539  
DATED : March 29, 2011  
INVENTOR(S) : Manfred Windisch, Birgit Hutter-Paier and Robert Wronski Page 1 of 1

It is certified that error appears in the above-identified patent and that said Letters Patent is hereby corrected as shown below:

Title page, item (22) should read as follows:

--(22) Filed: December 5, 2007--

Signed and Sealed this  
Seventh Day of June, 2011

David J. Kappos  
*Director of the United States Patent and Trademark Office*